United States Patent
Ross

(10) Patent No.: US 8,999,254 B2
(45) Date of Patent: Apr. 7, 2015

(54) CADAVER DISPOSAL SYSTEMS

(75) Inventor: Brandon F. Ross, Brownsburg, IN (US)

(73) Assignee: BioSafe Engineering, LLC, Brownsburg, IN (US)

(*) Notice: Subject to any disclaimer, the term of this patent is extended or adjusted under 35 U.S.C. 154(b) by 932 days.

(21) Appl. No.: 13/069,646

(22) Filed: Mar. 23, 2011

(65) Prior Publication Data

US 2012/0245402 A1 Sep. 27, 2012

(51) Int. Cl.
*B09B 3/00* (2006.01)
*C12M 1/00* (2006.01)

(52) U.S. Cl.
CPC .............. *C12M 45/06* (2013.01); *B09B 3/0075* (2013.01); *Y10S 588/90* (2013.01)

(58) Field of Classification Search
USPC ................................ 422/184.1; 588/412, 900
See application file for complete search history.

(56) References Cited

U.S. PATENT DOCUMENTS

| 6,437,211 | B2 | 8/2002 | Kaye et al. | |
| 6,472,580 | B2 | 10/2002 | Kaye et al. | |
| 7,183,453 | B2 | 2/2007 | Wilson et al. | |
| 8,133,716 | B2 * | 3/2012 | Shin | 435/262 |
| 8,283,512 | B1 * | 10/2012 | Maganas | 588/313 |

* cited by examiner

*Primary Examiner* — Edward Johnson
(74) *Attorney, Agent, or Firm* — Woodard, Emhardt, Moriarty, McNett & Henry LLP

(57) ABSTRACT

Apparatus and a method for decomposing a body of a deceased person, as an alternative to traditional cremation. The apparatus includes a primary vessel where the body is treated with a highly basic solvent to render the body into skeletal remains and liquid remains. A clamp is applied to the skull during processing for solvent access to the skull. A secondary vessel is used to receive the liquid remains from the primary vessel and further treat them. During this further treatment, the skeletal remains left in the primary vessel after the liquefied portion has been transferred to the secondary vessel, can be treated to be decolorized and deodorized, and then returned to the decedent's next of kin as ash-like material.

9 Claims, 7 Drawing Sheets

US 8,999,254 B2

CADAVER DISPOSAL SYSTEMS

BACKGROUND

Currently, widely used methods for taking care of human bodies after a person has died are burial in a cemetery, placement in a mausoleum or cremation. A person's body should be handled respectfully in any case. These methods have been used throughout history. Burial has grown to be very costly with the cost of the casket and plot of land for the burial. In some places there is a shortage of land for use as cemetery plots that increases the burden to those who wish burial. A decrease in the number of burials may result in an increase in the demand for cremation. However, there are issues with cremation. Although originally thought to offer an efficient and relatively clean process, the consequences of cremation have become increasingly apparent. For example, it is reported that 40% of the mercury emissions in the United Kingdom are due to cremation of human remains because of the mercury present in dental fillings. Also, cremation adds to the amount of greenhouse gases, from not only the body itself, but from a large amount of fuel needed to incinerate the body during cremation. The amount of fuel needed also makes the cremation process energy intensive, which is a concern because of the rising energy costs. Therefore, there is a need for an alternative method to either burial or cremation for taking care of a deceased person's body.

Some systems exist for the highly basic hydrolysis method of reducing organic materials to constituent parts. U.S. Pat. Nos. 7,183,453, 6,472,580 and 6,437,211 describe methods for treatment of organic materials, such as medical waste, with highly alkaline solutions to convert the organic materials into sterile solutions and solids. Commercial systems utilizing these methods are available to handle medical and animal waste products and ensure complete digestion and sterilization of the waste before disposal. These commercial systems, however, would not provide the respect to a deceased person's body and would lack the dignity with which human funeral situations necessarily need to be handled. Also, these systems may not work fast enough to be able to be employed effectively within the funeral parlor/crematorium setting.

SUMMARY

The present invention provides systems and techniques for the disposition of biological tissue, including the body of a deceased person, by chemical hydrolysis. While the actual nature and scope of the invention covered herein can only be determined with reference to the claims appended hereto, certain aspects of the invention that are characteristic of the embodiments disclosed herein are described briefly as follows.

According to one aspect of the invention, there is a biological tissue digester, comprising a sealable primary chamber constructed and arranged to receive a body for partial digestion, and a sealable secondary chamber constructed and arranged to receive digestion products from the primary chamber. Following receipt of digestion products from such primary chamber, the secondary chamber operates substantially independently of the primary chamber. In one refinement, the digester system includes a bone shadow reclamation basket with sides and a bottom designed to hold a human body for reception in the primary chamber. In an additional refinement, the basket is received in the primary chamber on rails attached on the inside of the primary chamber. In an additional refinement, agitation of treatment chemicals is done by sealed pump and distribution system. In another refinement, the system includes a skull clamp designed to apply an effective force to the skull of a body to be digested.

In another aspect, an apparatus for chemical treatment of biological tissue comprises a sealable primary chamber, a basket designed to hold the tissue, and a mounting system attached inside the chamber, to receive the basket, and a secondary chamber to receive material from the primary chamber. In a further refinement, the apparatus includes a device to determine the mass of tissue placed in the primary chamber.

In a further aspect, a method for chemical digestion of cadaver portions is provided, comprising placing a body into a first chamber, restraining the head of the body, applying a force to the outside of the head of the body, directing the force towards the inside of the skull, covering the body with an effective amount of a highly alkaline solution, heating to a predetermined temperature and agitating the highly alkaline solution, continuing to maintain a predetermined temperature, and agitating the solution for an effective amount of time until a desired amount of the organic material of the body has been liquefied, removing from the first chamber, the resultant liquid of the interaction of the highly alkaline solution with the body, rinsing the undigested skeletal remains of the body in the first chamber with a fresh liquid, drying the skeletal remains of the body, and removing the skeletal remains of the body and reducing them to a powder-like consistency. Meanwhile, the resultant liquid which was removed from the first chamber is moved to a second chamber where heating and agitation of it is continued for sufficient time to complete digestion. Following that, a pH adjustment of the liquid may be made suitable for disposal of the liquid in a sanitary sewer or otherwise.

These and other aspects are discussed below.

DETAILED DESCRIPTION

Figure 1:
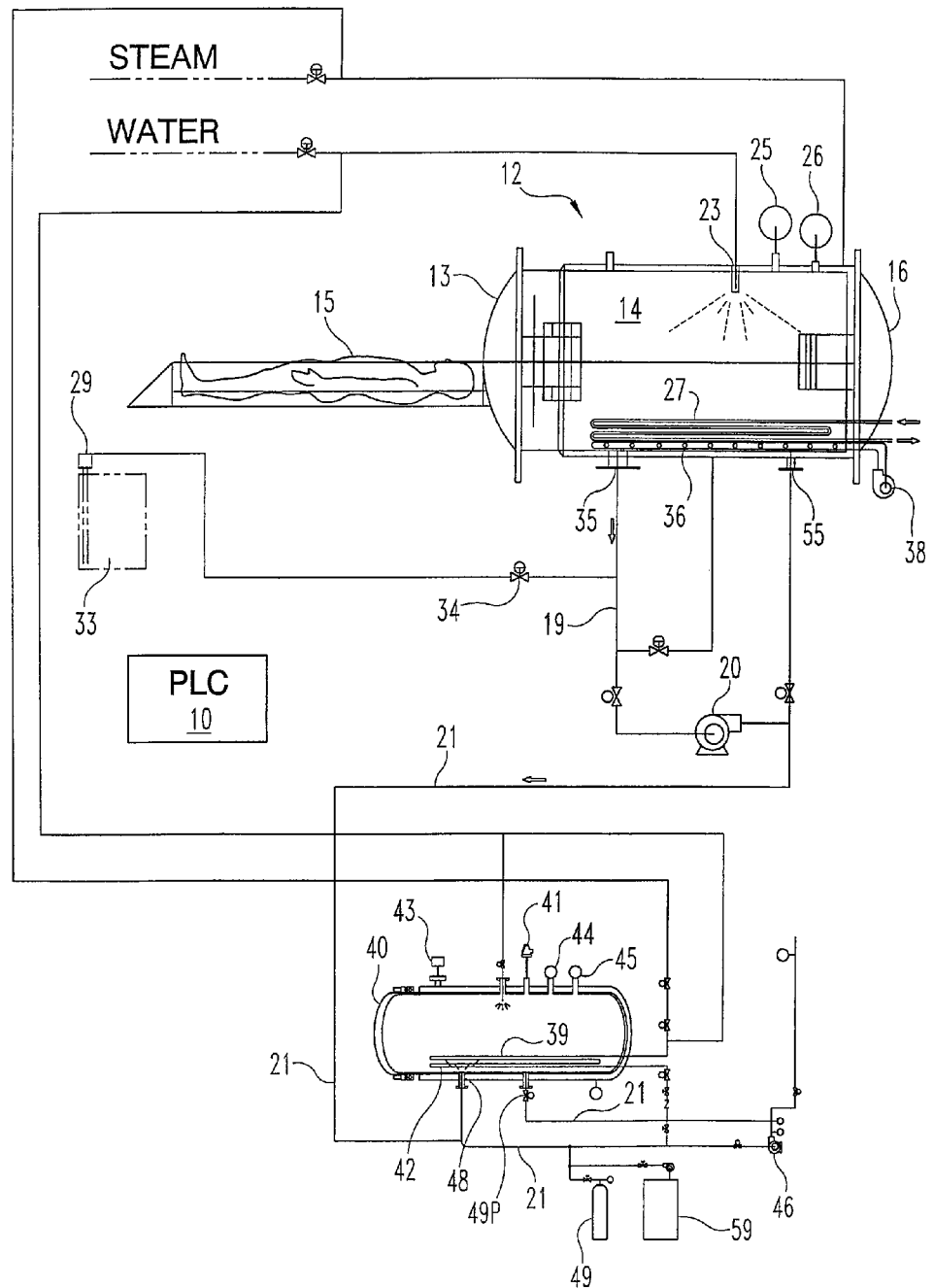
FIG. 1 is a general schematic representation of the hydrolysis system, showing primary and secondary vessels.

For the purposes of promoting an understanding of the principles of the invention, reference will now be made to the embodiment illustrated in the drawings and specific language will be used to describe the same. It will nevertheless be understood that no limitation of the scope of the invention is thereby intended.

Overview

The treatment described in the present disclosure is human body tissue hydrolysis with a strong alkaline solution to render the deceased body into constituent parts, only leaving skeletal fragments, "bone shadows", and a liquid portion that can be saved, if useful for other purposes, but more likely disposed of properly. The "bone shadows" are calcium phosphate forms of the bones. They are very porous and so they are very light, brittle and easily crumbled. They can be returned to the decedent's next of kin.

For the purposes of this application, a "highly alkaline solvent" or "highly basic solvent" may include, for example, 0.1 M to 2.5 M, optionally 0.5 M to 1.5 M, an aqueous solution of an alkali metal hydroxide, or an alkaline earth metal hydroxide. An aqueous solution of sodium hydroxide (NaOH—also commonly known as caustic soda or sodium hydrate) or potassium hydroxide (KOH—also commonly known as caustic potash or potassium hydrate) is preferred. Solutions containing calcium oxide (CaO—also commonly known as burnt lime, calx or caustic lime), ammonium hydroxide ($NH_4OH$—also commonly known as aqua ammonia) or magnesium hydroxide are suitable for some applications. An example of a suitable highly basic solvent may consist of a 0.1 M to 2.5 M solution of NaOH in water, or approximately 0.4%-10% sodium hydroxide (by weight) in water.

For treatment, the body is placed in a bone shadow reclamation basket. The entry door of a primary pre-treatment vessel is opened, the basket is placed inside, and the door is closed, sealing the vessel. A control system receives input from load cells located under the vessel, to determine the weight of the body tissue loaded in the basket. The body is treated with a sufficient amount of highly alkaline solvent such that the body may be rendered into its constituent parts, only leaving skeletal fragments and a liquid portion. A sufficient amount of solvent is given by adding a minimum of 0.1 M solution of NaOH 50% or KOH 45% as well as a minimum amount of water as to meet a 1 to 1 ratio of the tissue weight and the water weight. These ratios are given only as instruction as to how to conduct the method and operate the system stated herein and not to limit the nature or scope of the invention; one using the system and method described herein may find ratios more economical and exact as the invention is practiced. The water and hydroxide are introduced to the closed vessel by injectors or otherwise if desired by the operator.

If the reaction between the body and the highly basic solvent were allowed to proceed at its natural rate at room temperature, it may take an impractical amount of time. Therefore, it is advantageous to increase the reaction rate beyond its natural progression. One way to increase the speed of the reaction process is to heat the solvent, preferably to a temperature in the range of 150° F. to 400° F. The time of treatment at the elevated temperature can be in the range of 30 minutes to 4 hours, preferably 40 minutes to 60 minutes. Conducting the reaction in a sealed vessel allows an increased pressure to be used so that a higher temperature can be achieved to reduce the reaction time needed to digest the body. One mode of treatment is to heat the solvent to at least 300° F. and hold it at that temperature for at least 60 minutes. During the heating, the liquid contents of the vessel should be agitated to better mix the hydroxide and water with the tissue. Agitation may be by external pump, internal agitators, or otherwise. The amount of agitation can be controlled to allow for varying degrees of bone structure to remain intact for removal after the process has been completed. The amount of bone shadows that will remain can vary from as much as being completely intact to being completely dissolved in the primary vessel processing for separation via centrifuge for fast processing. After the contents of the primary vessel have been maintained at a minimum temperature of 300° F. for a period of no less than 30 minutes, a diversion valve will open and direct the resultant flowable contents of the primary vessel to a secondary processing vessel.

Utilizing a separate vessel to complete the treatment of the transferred liquid enables further processing of the skeletal remains in the first vessel separately from the liquid transferred from the first vessel to the secondary vessel for processing the liquid in the second vessel.

The transferred material treatment is completed in the second vessel by continued heating and agitating the liquid in the second vessel for some additional time to ensure that the flowable material has been completely digested. The additional time may be up to four hours or more, but preferably, 60 minutes to 2 hours. The temperature of the treatment of the material in the secondary vessel will be nearly the same as utilized in the treatment of the body in the primary vessel. The pH of the liquid can then be adjusted to a desirable level so that it may be cooled and properly disposed as into a sanitary sewer, or otherwise. For example, by introducing $CO_2$ gas or liquid into the liquid, the pH of the liquid may be lowered. However, other methods of pH adjustment may be used. An example is using mineral acids.

Except for transfer of the flowable, preferably liquid, digestion product, the primary and secondary vessel will operate independent of each other. Therefore, for a certain body, if completion of treatment to the point of removal of the bone shadow from the primary vessel takes longer than completion of the treatment of resultant liquid in the secondary vessel, the treated liquid can be disposed of in a sanitary sewer. Then a liquid resultant from a different body treated in a different primary vessel can be transferred to this secondary vessel and treated while treatment of the skeletal remains of the first body in the first primary vessel is being completed. This allows for the handling of more bodies during a specific time frame, which will make the treatment process more economically feasible, but without risk of mixing the skeletal remains.

Apparatus Details

Now turning to FIG. 1, a primary processing vessel 12 is provided with a front door 13 to chamber 14 to receive the body 15 for treatment. The body is supported in a basket 50 which is porous throughout. In the event the body is incomplete because of separation and loss of parts in fire, accident or otherwise, the basket is used for all of the body parts that remain. The door 13 is opened, and the basket is moved into the doorway and is received on rails 28 (FIG. 4A) fixed to the interior side walls of the vessel 12 and which extend from the door opening back to the closed end wall 18 of the vessel 12.

A second processing vessel 40 is arranged to receive liquid from the primary vessel 12 after a first part of the treatment has been completed in the primary vessel. The treatment resultant liquid can be transferred from the primary vessel to the secondary vessel through lines 21 by gravity 19, pumping 20, through pressure differential between the primary and secondary vessels (pressure transfer), or any other method suitable. The vessels must be constructed from material capable of withstanding the pH levels, temperatures and pressures employed in the hydrolysis process or treatment.

Suitable materials for the vessels include certain formulations of stainless steel or even carbon steel, but other materials resistant to the processing conditions can be used. The primary vessel door 13 is capable of being closed so that it is pressure and airtight, to withstand the temperatures and pressures of the hydrolysis treatment and prevent the escape or inadvertent exhausting of the contents from the vessel interior to atmosphere, as well as to prevent atmospheric carbon dioxide from entering the vessel during treatment. Such closure of the primary vessel 12 may be achieved by conventional door locking mechanisms or door clamps 22 well known in the industry, and whereupon the door is locked and sealed shut.

The hydrolysis system may be controlled by a conventional programmable logic controller (PLC) system 11 (FIG. 1) for automated operation, and a keyboard for alternative manual input or operation. The use of a computer controlled PLC (programmable logic controller) will facilitate the ease of operation of the apparatus described in this disclosure, making it amenable for use in a mortuary setting. It can be programmed for performing the treatments as desired by the system operator.

The system further may include a mass transducer such as, for example, load cells 81 (FIG. 4) coupled to the primary vessel 12 for determining the mass of the body received within the primary vessel and for generating an output signal to the PLC, indicating such mass data. The transducer is preset such that the mass of the primary vessel with a bone reclamation basket but without a body present, equals zero. The contents mass data may then be entered into or read by the PLC control system for determining the appropriate amounts of water and alkali to introduce into the interior 14 of the primary vessel 12.

The primary vessel 12 (FIG. 1) also can have internal injectors such as 23 to spray water reactants, or rinses, over a body in the primary vessel 12. The reactants are strong alkali solution for hydrolysis of the body as well as hydrogen peroxide or some other bleaching or deodorizing agent to treat the skeletal remains after the hydrolysis is complete. The rinse material in most cases is water, but this and other injectors can be used for other materials as well. In addition, the primary vessel 12 may be equipped with temperature sensing 25, pressure indicator 26, liquid level, and other sensing and monitoring devices. Such sensing and monitoring devices are known in the art for use with chemical processing equipment.

The primary vessel 12 may be heated by external heating jacket, internal steam coils 27, electrical heaters or some other heating device such as is known in the art. The fluid contents in the primary vessel 12 are agitated by a mechanically sealed pump 36 and plumbing system 38 to distribute the processing liquids in the vessel, but agitation can be done through the use of an internal mechanical agitator or otherwise.

Figure 4A:
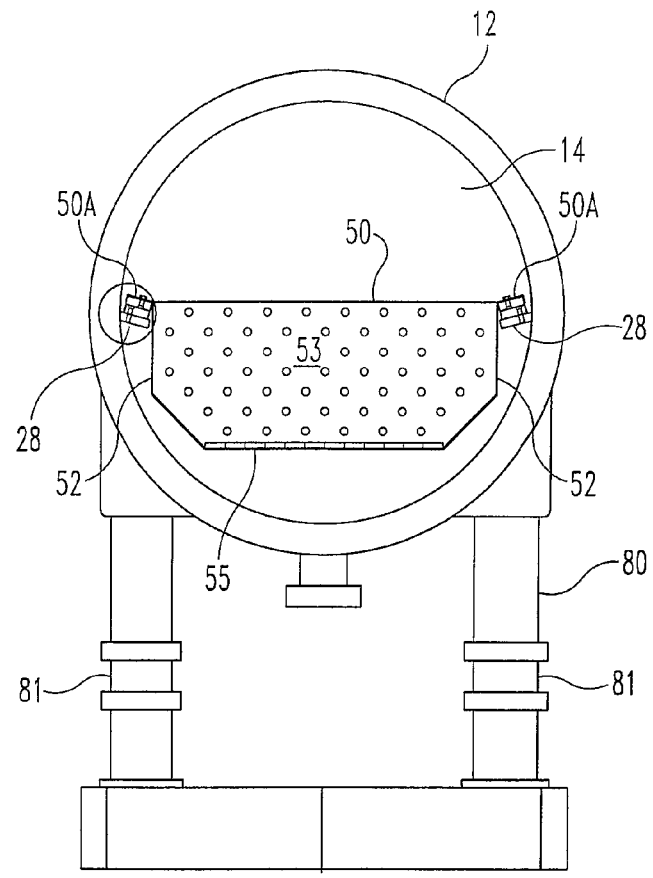
FIG. 4A is a view of the front end of the primary vessel of FIG. 1 (with the front door and hinges eliminated for simplicity, but showing the end of the basket received on the support rails, and showing the primary vessel mounted on a support stand) to facilitate entry and removal of the basket by a system operator.
Figure 4B:
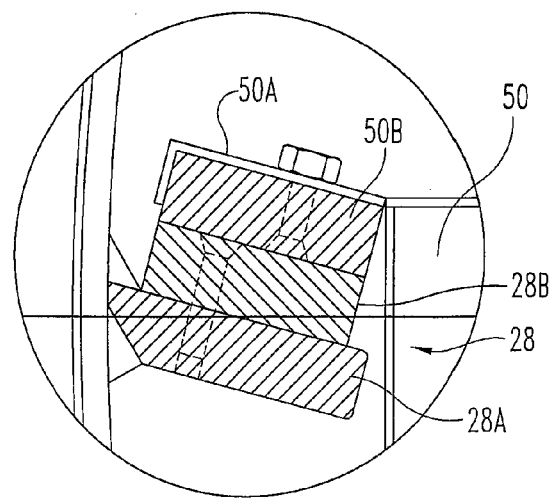
FIG. 4B is an enlarged fragment of FIG. 4A and showing details of a basket support rail with basket thereon.

FIG. 4A is a view of the primary vessel 12 along its longitudinal axis, showing the vessel secure on a cradle which has four legs 80 (two of the four being shown, the other two being hidden behind them) which support the vessel at a height facilitating the work. The view is into the open door end of the primary vessel 12 (door and hinges omitted to simplify the drawing) with the basket 50 supported in place on rails 28. As shown in the enlargement FIG. 4B, each rail has a support plate 28A welded along the inside wall of the vessel. A bearing strip 28B is fastened to the top of plate 28A along the length of the plate. As described below, there is an L-shaped flange 50A extending the full length of the basket, and to which a bearing strip 50B, Teflon, for example, is fastened along the length of the flange. The fastenings of members 28B and 50B can be done by fasteners as shown, or by other means if found suitable for the harsh environment generated in the vessel 12 during treatment. The bearing strips may be of materials suitable for low friction sliding of the basket on the rails 28 for moving the basket into the vessel 12 for treatment of the body, and for removal of the basket from the vessel following the treatment.

Figure 5:
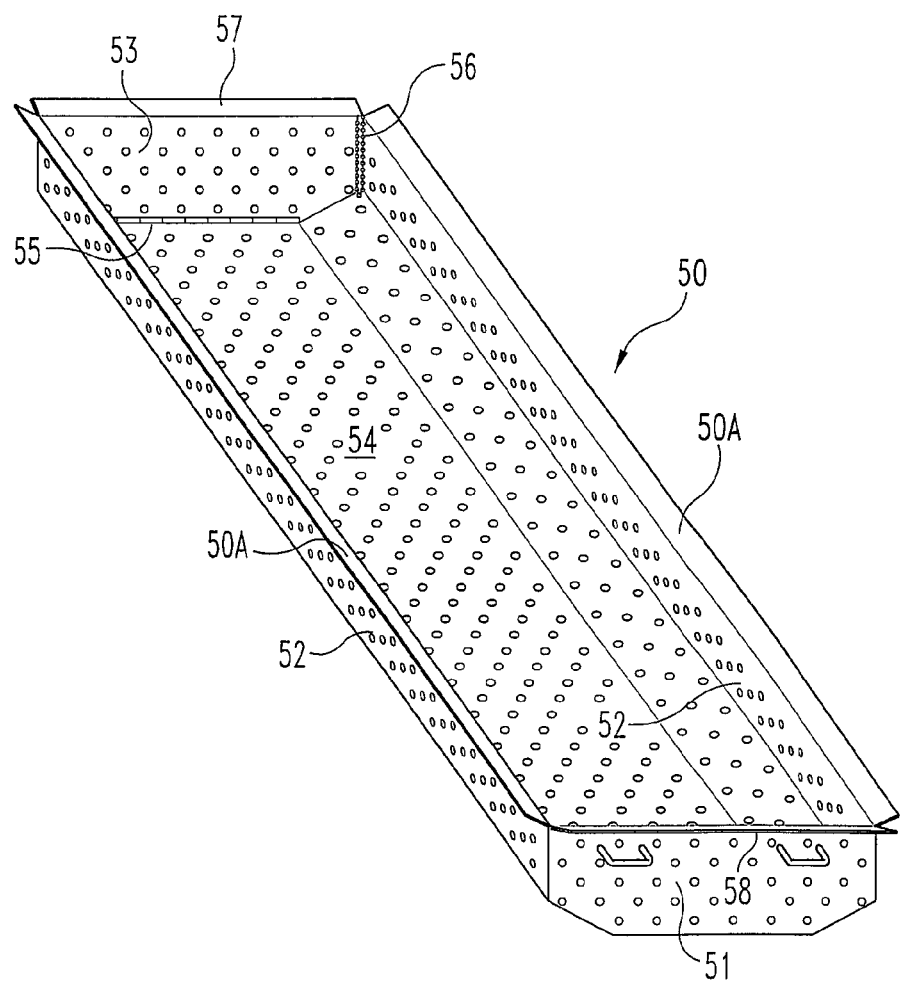
FIG. 5 is a perspective view of the body basket.

Referring to the FIG. 5 perspective view of the basket 50, it should be sturdy enough to hold a human body and withstand manual loading of the body into the basket, as well as manual handling of the loaded basket into the primary vessel. It is desirable that it be usable with an automatic or assisted loading system. For an example of material, but without limiting choices, the basket may be made of sixteen gauge stainless steel material, perforated or mesh to allow the free flow of the digestion fluid through the basket and around the body to be digested. As an example for perforations, ⅜ inch diameter holes at ½ inch staggered centers is suggested. The basket has a closed end 51 which is the front end for leading into the primary vessel for the treatment process. The sides 52 extend to a rear end wall 53 of the same kind of material and which is mounted to the bottom 54 by a piano-type hinge 55 so the rear end wall can be dropped-down to allow dry skeletal remains to be removed from the basket without removing the basket 50 from the primary vessel 12, if desired. A window or door sash chain 56, for example, can be fastened to the top of the basket side 52 and to the top of the rear end wall 53 to limit the distance of the drop of the top of the end wall to horizontal when released for removal of the remains from the basket. If desired, this feature can be used with the basket empty before processing, for sliding the body lengthwise into the basket.

Figure 2A:
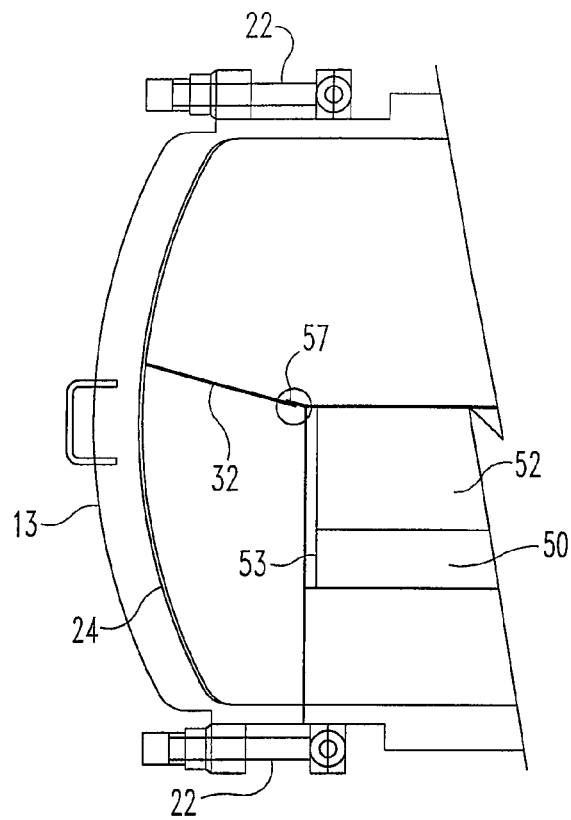
FIG. 2A is an enlarged longitudinal sectional view of the entry door and of the primary vessel of FIG. 1 with the door closed and an empty body basket in place inside.
Figure 2B:
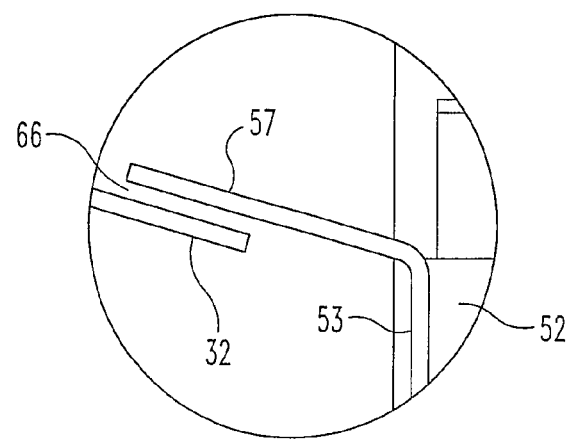
FIG. 2B is an enlargement of a portion of FIG. 2A.
Figure 3A:
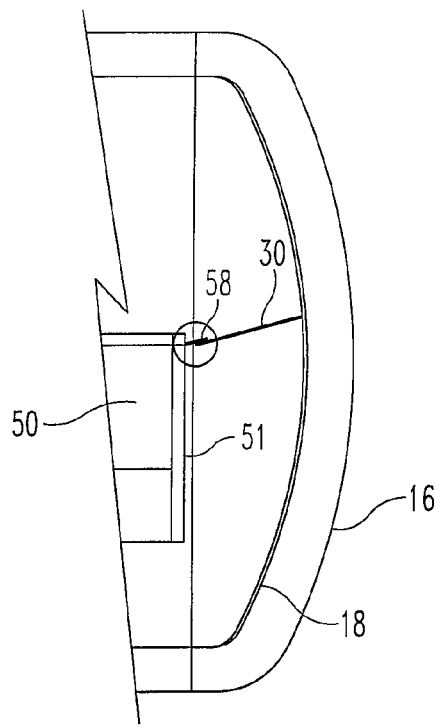
FIG. 3A is an enlarged longitudinal sectional view of the vessel back and opposite the door.
Figure 3B:
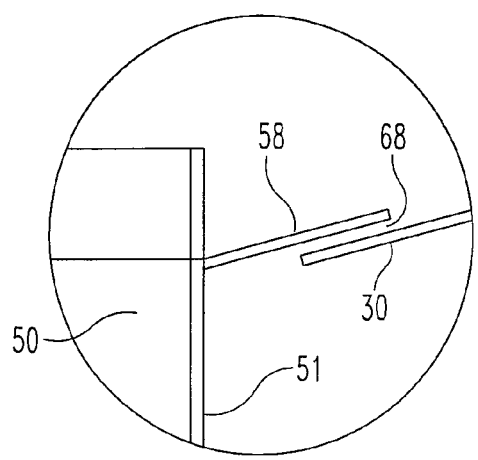
FIG. 3B is an enlargement of a portion of FIG. 3A.

Provisions are made in the primary vessel and on the basket to inhibit movement of partially decomposed materials, solid or semi-solid, from floating over the sides of the basket and toward the bottom of the vessel during processing. For this purpose, there are features on the vessel walls overlapping features of the basket when the basket is in position in the vessel for processing the body. For example, referring to FIGS. 2A and 2B there is a plate 32 fixed to the inside face 24 of the door 13 and which extends across the width of the door. On the basket there is a flange 57 extending outward and upward at the top of the basket wall 53 and which extends across the width of the basket. Similarly, as shown in FIGS. 3A and 3B, there is a plate 30 fixed to the inside face 18 of the closed end 16 of the primary vessel and extending across the width of the vessel. There is an upwardly and outwardly extending flange 58 at top of the basket closed end wall 51. At the door end of the vessel, the flange 57 of the basket overlaps the plate 32 of the vessel (FIGS. 2A and 2B). At the closed end of the vessel, the flange 58 on the closed end of the basket overlaps the plate 30 fixed to the vessel. Both of these relationships of basket flange to vessel plate established when the basket is fully inserted into the primary vessel 12, provides a sort of barrier to inhibit solid materials from leaving the ends of basket 50 and falling to the bottom of the primary vessel 12 during the hydrolysis procedure. While the gaps 66 (FIG. 2B) and 68 (FIG. 3B) at the overlaps, inhibit travel of solids toward the bottom, they allow any fluid in their vicinity to drain back to the primary vessel bottom. Also, the relationship of the upward and outward side flanges 50A of the basket overlapping the rails 28 (FIGS. 4A and 4B) prevents solids from overflowing sides of the basket to the bottom of the primary vessel 12.

These relationships may be considered in a way to effectively divide the primary vessel internal volume 14 into an upper portion and a lower portion. This interface is produced through basket side rails 50A being supported on the primary vessel side rails 28, and the overlap of the closed end vessel divider extension plate 30 and the basket closed end divider extension flange 58, and the overlap between the vessel door divider plate 32 and the basket hinged end divider extension flange 57.

Figure 6:
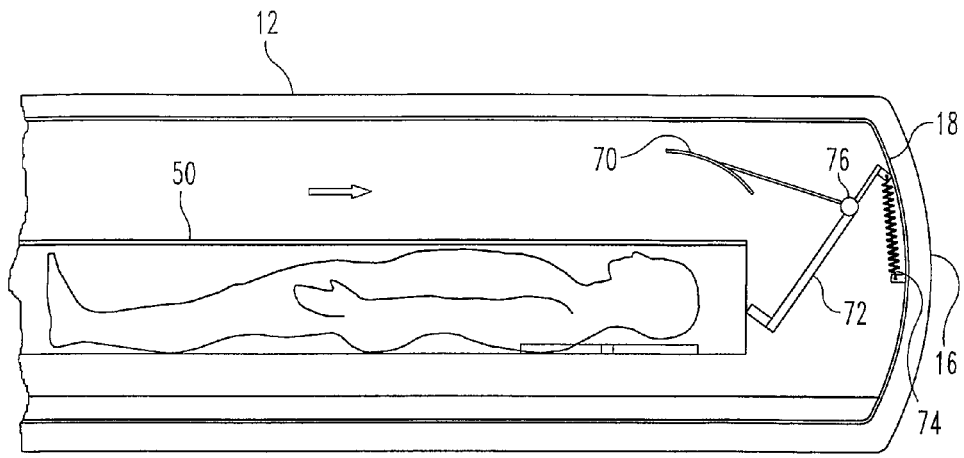
FIG. 6 is a longitudinal sectional view of a portion of the primary vessel with the basket containing the cadaver while the basket is being moved into place for treatment.
Figure 7:
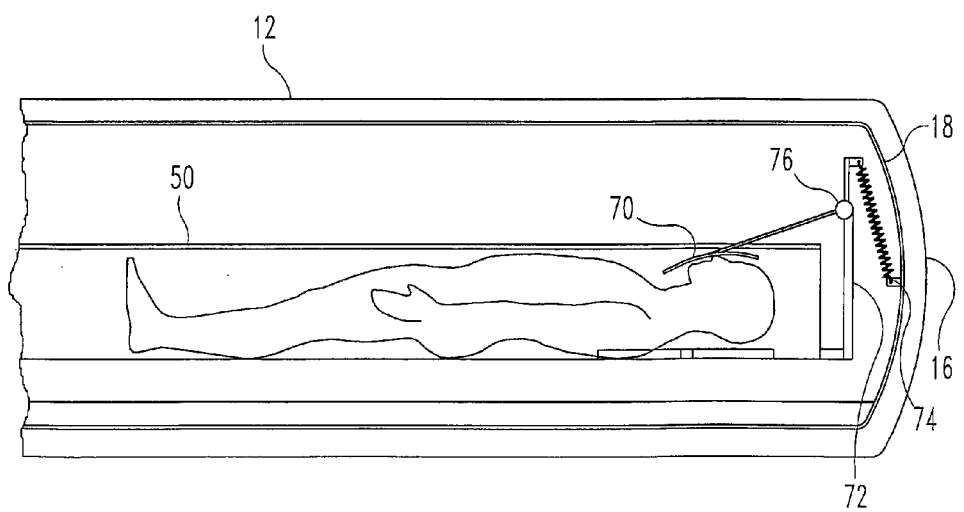
FIG. 7 is a view like FIG. 6 but with the basket in place engaging the head of the cadaver for fracturing the skull.

Referring now to FIGS. 6 and 7, FIG. 6 is a side view with the basket 50 in the primary vessel 12 just touching a lever arm 72 of a head restrainer clamp 70. The lever arm 72 is pivotally mounted to the inside of the primary vessel 12 at the closed end 18. Arm 72 is connected to a spring 74 which biases the lever arm 72 so that the head restrainer clamp 70 attached to the arm 72 is in a first position (FIG. 6) away from the basket so that the basket 50 may be slid fully into primary vessel 12. The basket 50 will contact the lever arm 72 while sliding into the primary vessel at a first position near the closed rear end of the vessel. Upon further sliding of the basket 50 into the primary vessel 12, the basket end will push the lever arm 72 to rotate it about pivot point 76 causing the head clamp 70 to move downwards towards a second position and make contact with the head of the body held in the basket 50. When the basket 50 is completely slid into the primary vessel 12, the lever arm 72 and head clamp 70 will have moved to the second position (FIG. 7), where the head clamp 70 contacts and bears down on the head of the body in the basket 50 with a force so that, when the skull is softened during the hydrolysis process, the force is effective to deform and breach the skull to allow hydrolysis treatment fluid to enter the skull cavity. The plate 30 and basket flange 58 may be slotted to accommodate the movement of lever arm 72.

Alternate devices can be envisioned that will restrain the head of a body in the basket and apply pressure to the skull to cause deformation when the skull has been weakened by hydrolysis. Examples are a band about the skull and tensioned by one or more springs, or one or more pieces of elastomeric material. The springs or elastomeric material will provide the force necessary to breach the skull during treatment. The band can either attach around the head or may be connected to the basket. Suitable materials for the band and springs include certain formulations of stainless steel, carbon steel or polymers like polytetrafluoroethylene, but other materials that will not be degraded by the hydrolysis conditions can be used. Elastomeric material needs to be resistant to the processing conditions. EPDM rubber (ethylene propylene diene monomer rubber) is an example.

The secondary vessel 40 (FIG. 1) is shown elongate in a horizontal attitude but a vertical configuration or other shape could be used if desired. The secondary vessel 40 is arranged to receive the digestion resultant material from the primary vessel 12 after sufficient time has passed for the fleshy part of a body to be treated and converted to mostly liquid in the primary vessel. The secondary vessel 40 is constructed of either stainless or carbon steel, but other material that can resist the processing conditions can be used. The secondary vessel 40 is normally closed so that it is pressure and airtight, to withstand the temperatures and pressures of the hydrolysis treatment process and prevent the escape or inadvertent exhausting of the contents of the vessel to atmosphere, as well as to prevent atmospheric carbon dioxide from entering the vessel during treatment. Such closure of the secondary vessel 40 may be achieved by conventional sealing and clamping well known in the industry (not shown). It will also be equipped with a vent valve 41 that will vent excess pressure during the process, and a vacuum break 43 to alleviate vacuum conditions when material is exiting the secondary vessel 40. In addition, the secondary vessel can be equipped with temperature sensing 44, pressure indicator 45, liquid level, weight sensing and other devices (not shown) to facilitate operation and monitoring and safe operation of the process. The treatment resultant liquid in secondary vessel 40 may be agitated via a mechanically sealed pump 46 and plumbing system 48 to distribute this effluent transferred from the primary vessel. This secondary vessel 40 is heated or cooled via internal coils 42 but other temperature control devices may be used such as an external jacket or an external heat exchanger. Devices and equipment not shown are well known in the art. Except for reception of digestion resultant liquid transferred from the primary vessel for further digestion, the secondary vessel 40 operates totally independently of the primary vessel 12, and can also be controlled by the same PLC 10 connected to the primary vessel 12, or by a separate PLC. The secondary vessel 40 can be operated at the same time as the primary vessel 12 is finishing its work on the skeletal remains of the body.

Figure 8:
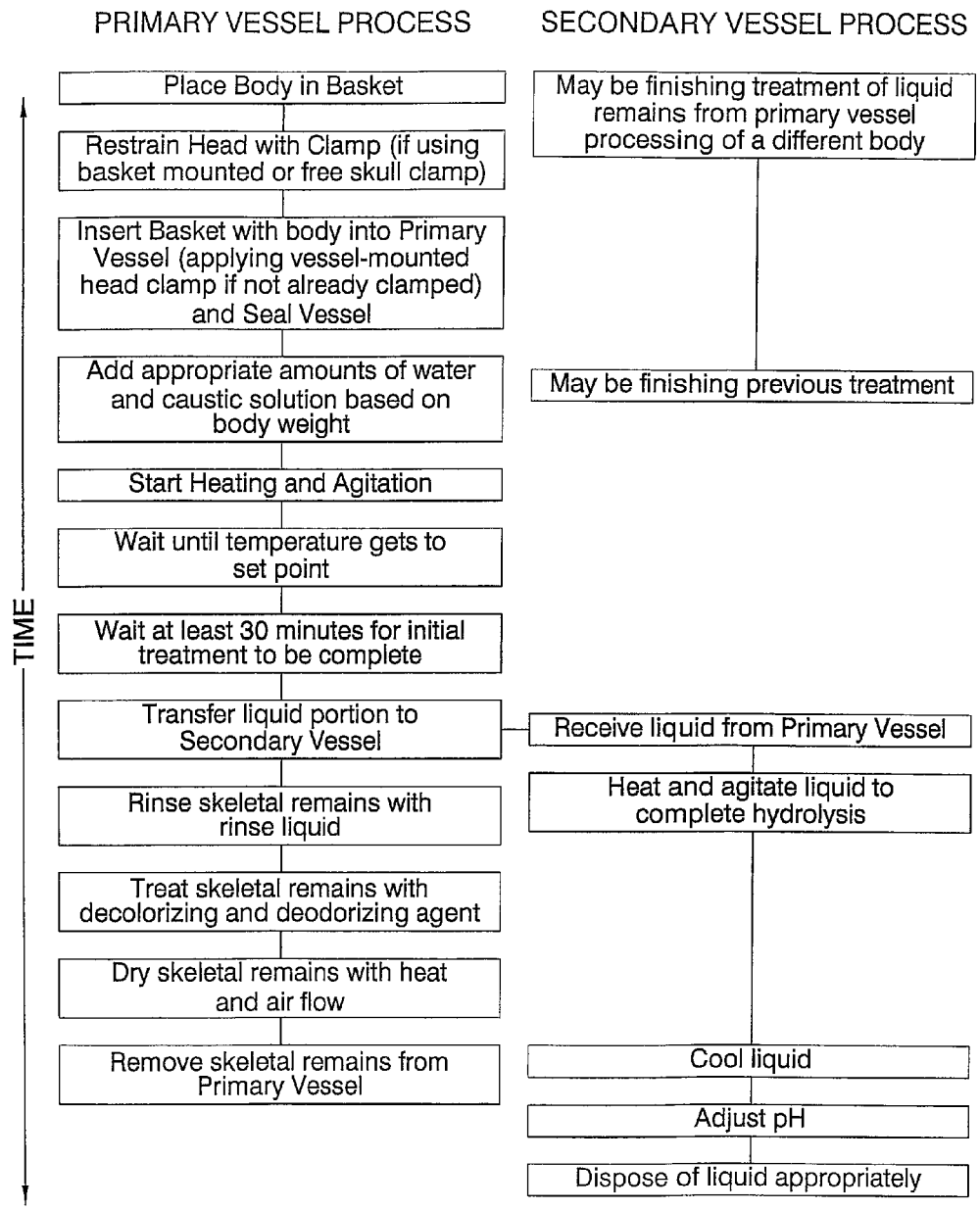
FIG. 8 is a flowchart representing the method for treating a cadaver according to the illustrated embodiment of the invention.

A block diagram overview of the process is presented in FIG. 8. As indicated above, processing in the secondary vessel may overlap with processing in the primary vessel. In fact, completing the treatment of liquid digestion products from a previous body may continue in the secondary vessel while treatment of another body is started in the primary vessel, as indicated by the steps in FIG. 8 under the secondary vessel heading: "May be . . . body". Each vessel will operate independent of each other so that processing of different bodies at the same time is possible without mingling of body constituents.

Now for one body, it is placed in the basket 50 manually or by an automated transfer system. Once the body has been placed into the basket, the door 13 of the primary vessel 12 will be opened and the basket will be slided into the vessel and the door will be closed. Once the door to the vessel has been closed and secured by clamps 22, for example, the control system will utilize the mass measuring device, such as one or more load cells 81 (FIG. 4), located below the primary vessel at the four legs 80, to determine the mass of the body that was loaded into the basket. Once the PLC control system has determined the correct mass of the body being processed, it will cause drum pump 29 to pump from hydroxide tank 33 through valve 34 and vessel port 35, a minimum of 0.1 M solution of NaOH 50% or KOH 45% into a minimum amount of water delivered into vessel 12 through injector 23, to meet a 1 to 1 ratio with the body mass and the water mass.

After the caustic and water has been added to the primary vessel the control system will then begin to heat the contents of the vessel using internal steam coils 27 or external heating elements such as a jacket on the vessel. A minimum temperature of 250° F. is preferred for the period needed, which might be 40 minutes, for example. During this time the liquid contents of the vessel will be agitated by an external pump 38 with internal distribution manifold 36. For the purpose of mixing the hydroxide and water about the body, internal mechanical agitators (not shown) might also be used. The amount of agitation can be controlled to allow for original bone structure to enable some to remain intact as "bone shadows" for removal after the process has been completed. The amount of bone shadows that will remain can vary from as much as being completely intact to being completely dissolved in the solution for separation via centrifuge for fast processing. After the contents of the vessel have been maintained at a minimum temperature of 250° F. for the necessary period, a transfer valve 37 will be opened and direct the liquid contents from the primary vessel to the secondary vessel.

Within the secondary vessel, the control system will continue to heat (steam in coil 39) and agitate the contents for a minimum of 1 hour to complete the digestion cycle. Once this is complete in the secondary vessel, the contents are cooled as by water in coil 39. At this point in the process, pH correction can be implemented using liquid or gas $CO_2$ injection from a tank 49 through plumbing into port 49P into vessel 40. As the $CO_2$ is added into the secondary vessel, the control system monitors the pH, temperature and pressure to determine when to stop injecting $CO_2$, based on the preset pH condition selected by the user for disposal. The contents of the secondary vessel are now ready for disposal to a sanitary sewer or elsewhere, if appropriate.

After the liquid contents of the primary vessel have been transferred to the secondary vessel, only an intact skeletal structure will remain in the primary vessel. While the above-described digestion processing of the transferred liquid is occurring in the secondary vessel, treatment of skeletal remains will continue in the primary vessel. The control system will perform a final heated rinse of the remains by utilizing the water spray system (injector 23) to clean the bones of any possible residual material. Once the final rinse has occurred, the rinse water will be cooled and drained to a sanitary sewer connection for disposal. Hydrogen peroxide ($H_2O_2$) injection may then be carried out for the purpose of odor control or bone whitening. This can be accomplished by pumping from drum 59 through a valve and some plumbing as used for the $CO_2$, but up to port 55 in primary vessel 12 that delivers the $H_2O_2$ directly into the primary vessel. The control system monitors the flow of the $H_2O_2$ via flow sensors to allocate the correct amount of $H_2O_2$ to the primary vessel. After the $H_2O_2$ has been introduced into the primary vessel for a period of 20 minutes, for example, or longer for bone whitening, the $H_2O_2$ solution may be drained to the sanitary sewer. If the $H_2O_2$ is injected only for odor neutralization, the contents may be drained immediately after the full amount of peroxide has been injected.

At this point the primary vessel vent valves will open and air will be drawn through the primary vessel for a period of 15 minutes to allow for the skeletal remains to evaporate some of the excess water that is trapped within the bones. A vacuum drying system may be incorporated into the vent section of the primary vessel, to be applied during the drying cycle of the process. The vacuum pump would act in aiding the drying process by lowering the pressure within the vessel as well as lowering vapor point of the liquid in the primary vessel. Once the bones have reached an acceptable level of moisture content, the door to the primary vessel may be opened and the reclamation basket may be removed. Once the bone shadows have been collected from the reclamation basket, they may be managed as instructed by the decedent's next of kin. If so desired, the bone shadows may be placed into a macerator/grinder to pulverize them for placement into an urn for return to the decedent's next of kin.

If the bones are not whitened by using $H_2O_2$, they may be sent through an ultraviolet (UV) processing auger for further whitening via UV light. $H_2O_2$ injection can also be accomplished within either process vessel for the purpose of odor control. The control system can monitor the flow of the $H_2O_2$ via flow sensors to allocate the correct amount of $H_2O_2$ to the selected process vessel.

While a preferred embodiment of the invention has been illustrated and described in detail in the drawings and foregoing description, the same is to be considered as illustrative and not restrictive in character. Modifications that come within the spirit of the invention described herein are desired to be protected.

The invention claimed is:

1. A biological tissue digester system, comprising:
a sealable vessel constructed and arranged to receive a cadaver to be digested and discharge digestion product in flowable form the vessel including a bottom and parallel, horizontally-spaced rails attached to the inside of the vessel and spaced from the bottom of the vessel; and
a basket with sides and a bottom and supported on the rails of the vessel and spaced from the bottom of the vessel to hold a human body spaced from the bottom of the vessel.

2. The digester system of claim 1 wherein:
the basket has an end wall that is pivotally attached to the bottom of the basket.

3. The digester system of claim 1 wherein:
the sides and bottom of the basket define a multitude of holes.

4. The digester system of claim 1 and further comprising:
a skull clamp in said vessel positioned to apply sufficient force to a skull of a body in said basket to fracture said skull.

5. The digester system of claim 4 and including:
means to cause the skull clamp to automatically apply the sufficient force to the skull of a body held in the basket when the basket is fully received in the vessel.

6. A biological tissue digester system for use with a cadaver, comprising:
a reaction vessel;
a basket with sides and a bottom to hold a cadaver for reception inside the reaction vessel; and
a skull clamp with means to apply an effective force to fracture a skull of a cadaver held in the basket.

7. The digester system of claim 6 wherein the reaction vessel includes rails attached to the inside of the vessel which receive and support said basket inside the vessel.

8. The digester system of claim 6 wherein the sides and bottom of the basket define a multitude of holes.

9. The digester system of claim 6 and further comprising:
means in said reaction vessel for causing said skull clamp to automatically apply said force to a skull of said cadaver held in the basket, as the basket is fully received in the vessel.

* * * * *